United States Patent [19]
Mullinax et al.

[11] Patent Number: 6,030,840
[45] Date of Patent: Feb. 29, 2000

[54] NEUTRAL ENHANCEMENT OF LANTHANIDES FOR TIME RESOLVED FLUORESCENCE

[75] Inventors: Thomas Robert Mullinax, Newton, Mass.; Margaret R. Cody, Nashua, N.H.; Mark N. Bobrow, Lexington, Mass.

[73] Assignee: NEN Life Sciences, Inc., Boston, Mass.

[21] Appl. No.: 09/094,628

[22] Filed: Jun. 15, 1998

[51] Int. Cl.⁷ .................................................. G01N 33/20
[52] U.S. Cl. .............................. 436/82; 436/86; 436/172; 436/537; 436/546
[58] Field of Search ..................... 436/536, 537, 436/546, 82, 86, 172

[56] References Cited

U.S. PATENT DOCUMENTS

| | | | |
|---|---|---|---|
| 4,565,790 | 1/1986 | Hemmila et al. | |
| 4,808,541 | 2/1989 | Mikola et al. | |
| 4,920,195 | 4/1990 | Kankare et al. | 534/16 |
| 5,124,268 | 6/1992 | Dakubu | |
| 5,256,535 | 10/1993 | Ylikoski et al. | 435/6 |
| 5,316,909 | 5/1994 | Xu | |
| 5,373,093 | 12/1994 | Vallarino et al. | |
| 5,622,821 | 4/1997 | Selvin et al. | |
| 5,637,509 | 6/1997 | Hemmila et al. | 436/537 |

OTHER PUBLICATIONS

Kropf et al., *Analytical Biochemistry*, 1991, 197:258–265.
Dakubu et al., *Analytical Biochemistry*, 1985, 144:20–26.
Yeh et al., *Experientia*, 1979, vol. 35, pp. 715–716.

*Primary Examiner*—Jeffrey Snay
*Attorney, Agent, or Firm*—Rothwell, Figg, Ernst & Kurz

[57] ABSTRACT

A method for the spectroscopic determination of a marker comprises:

(a) contacting chelated lanthanide metal ions bound to a marker with a buffered solution comprising a detergent, an enhancer reagent and a polyanion, wherein the buffer maintains the pH of the solution within the range of about 3.5 to about 11.5 and the polyanion is present in sufficient concentration such that the lanthanide metal ion disassociates from the chelate complex and reassociates with the enhancer reagent, thereby transferring the lanthanide metal ion into fluorescent form; and (b) determining the amount of lanthanide metal ion liberated from the marker as a measure of the amount of marker present by subjecting the solution to a short radiation pulse and detecting the fluorescence of the lanthanide metal ion after the fluorescence from any background sources substantially has ceased.

33 Claims, 5 Drawing Sheets

NEUTRAL ENHANCEMENT OF LANTHANIDES FOR TIME RESOLVED FLUORESCENCE

BACKGROUND OF THE INVENTION

1. Field of the Invention

The present invention is directed to a method for the fluorescence spectroscopic determination of a biological marker containing bound lanthanide ions. More specifically, the invention is directed to such a method wherein the fluorescence of the lanthanide is enhanced by contacting the marker with a solution comprising a polyanion and an enhancer reagent, such that the lanthanide metal ions dissociate from the marker and reassociate with the enhancer reagent, thereby transforming the lanthanide metal ion into a highly fluorescent form. The amount of lanthanide metal ion which has been liberated from the marker and associated with the enhancer reagent then can be determined.

2. Prior Art

Lanthanide chelates are a preferred means of labeling detectors of biomolecules for time resolved fluorescence (TRF). A lanthanide metal ion, such as a europium or terbium ion, is coupled to a biological molecule of interest through a chelate-forming compound, such as ethylenediaminetetraacetic acid (EDTA) or an analogue thereof, and excited by a short radiation pulse. Detection of fluorescence of the marker is determined after the fluorescence from any background noise source has substantially ceased.

The lanthanide carrier-chelate can be either fluorescent or non-fluorescent. In either case, the lanthanide is rendered highly fluorescent via dissociation from the carrier chelate and subsequent enhancement through association with organic enhancer molecules.

One process that has been given commercial application is that disclosed in U.S. Pat. No. 4,565,790, issued to Hemmila et al. This patent teaches using an enhancer to dissociate the lanthanide from the carrier chelate by lowering the pH to less than 3.5. At such a low pH, the carrier chelate becomes protonated and no longer is capable of tightly binding the lanthanide. The lanthanide then can associate with a solution phase micellar organic enhancer and display intense fluorescence upon excitation.

Various literature references describe dissociative enhancers that work at acidic pH values or employ fluorescence-quenching amounts of urea and sodium dodecylsulfate (SDS). At pH values greater than 4, however, the lanthanide remains tightly bound and full fluorescent signal development may take hours or days.

An alternative process is that patented in U.S. Pat. No. 5,124,268, issued to Dakubu. In this method, an acid dissolution solution having a pH of about 2.0 is used to liberate the lanthanide. Then the addition of a higher pH solution containing enhancement reagents, such as β-naphthoyltrifluoroacetone (β-NTA), thenoyltrifluoroacetone (TTA), trioctylphosphineoxide (TOPO), etc., serves to neutralize the solution and allow association to the lanthanide with the enhancers in a fluorescent form.

Other methods for enhancement detection of lanthanide chelates use carrier chelates that directly excite the bound lanthanide (direct fluors). Exemplary compounds are found in U.S. Pat. Nos. 5,622,821 and 5,373,093. Such compounds can be used when localized signal information for the sample is important and/or when a homogeneous assay is required.

Although all of these methods can be useful, each has its drawbacks. The harsh conditions used for acid dissolution in the '790 patent usually disrupt association between the detector, capture reagent and analyte. The owners of the '790 patent, in literature regarding their commercial process, also have warned against using their enhancement solution with stronger chelates, such as diethylenetriamine pentacetic acid (DTPA). The procedure taught in the '268 patent does not suffer from these disadvantages, but is cumbersome in that it requires two sequential additions for detection and the signal generation is highly dependent on adding the correct amount of buffered enhancers to the acid portion. Undershooting or overshooting the desired final pH causes a reduction in the maximum fluorescence. In direct fluor methods, the fluorescence signal observed is about 20–1000 times less intense than the signal generated by enhancement reagents, limiting their use to assays where ultimate sensitivity is not required.

In view of the shortcomings of the known procedures, further improvements are sought.

SUMMARY OF THE INVENTION

In accordance with the present invention, a method for the spectroscopic determination of a chelated lanthanide ion bound to a marker comprises:

(a) contacting chelated lanthanide metal ions bound to a marker with a buffered solution comprising a detergent, an enhancer reagent and a polyanion (polyacid), wherein said buffer maintains the pH of the solution within the range of 3.5 to 11.5 and said polyanion is present in sufficient concentration such that said lanthanide metal ions disassociate from said marker and reassociate with said enhancer reagent, thereby transferring said lanthanide metal ions into fluorescent form; and (c) determining the amount of lanthanide metal ion liberated from the marker as a measure of the amount of marker present by subjecting the solution to a short radiation pulse and detecting the fluorescence of the lanthanide metal ion after the fluorescence from any background sources substantially has ceased.

DETAILED DESCRIPTION OF THE INVENTION

Figure 1A:
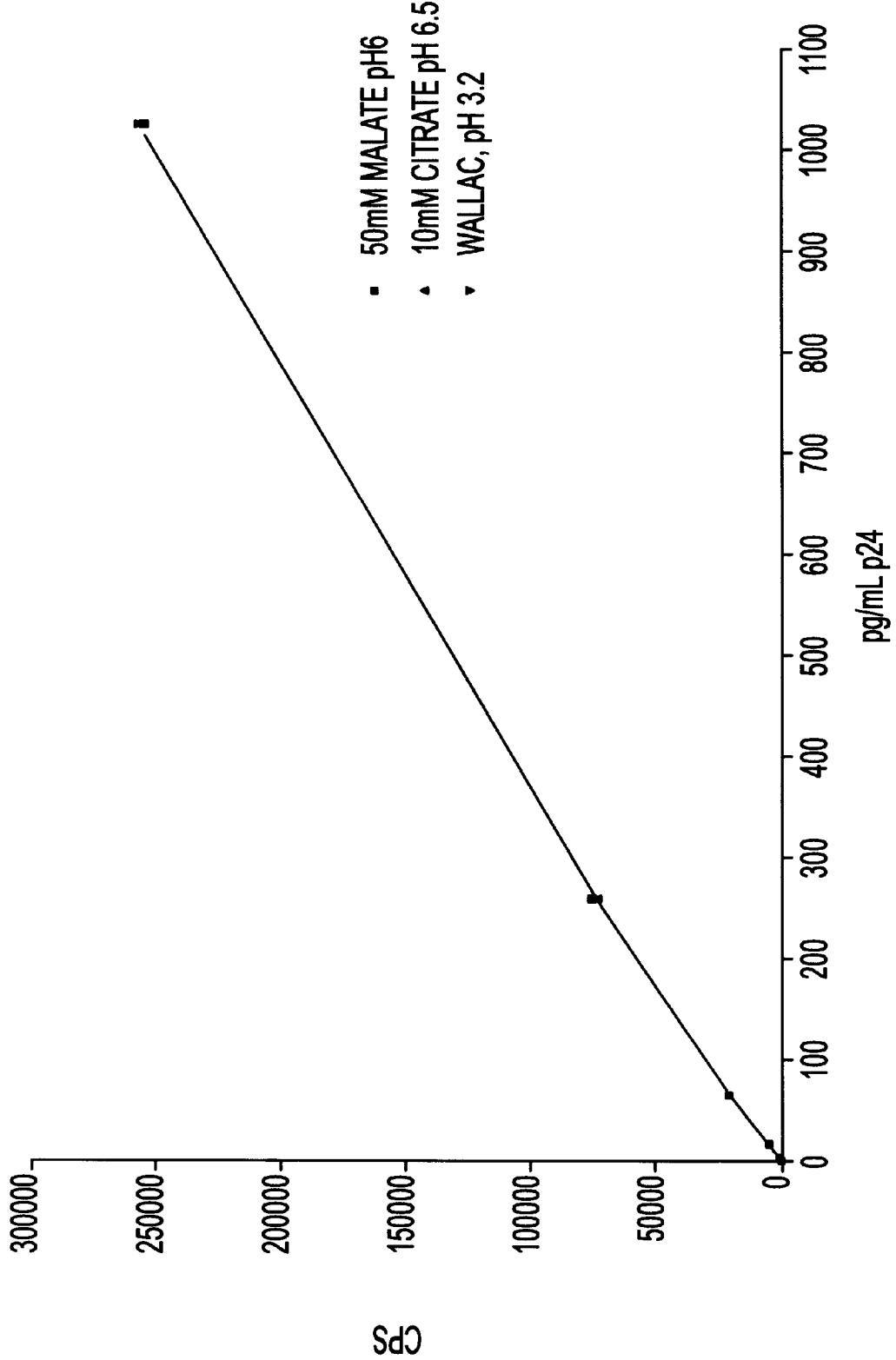
FIGS. 1A and 1B are graphs showing the results of a time resolved fluorescence determination of HIV-1 p24 antigen concentration in a sample using the method of this invention.

This invention presents a method for determining through fluorescent spectroscopic means the amount of a biological material present in a sample. In accordance with the method, a lanthanide metal ion bound to a marker through a chelating agent in a solution is separated from the marker by adding to the solution a detergent, an enhancer agent and an excess of a polyanion, wherein the polyanion is added in a sufficient amount to ensure that the lanthanide ion is quickly and completely released from the chelating agent and transferred into a highly fluorescent form through association with the enhancer reagent and measured by excitation by a short radiation pulse and detection of the fluorescence of the lanthanide ion following substantial cessation of fluorescence from any noise source.

A marker is defined as a member of a specific binding pair. Members of specific binding pairs suitable for use in practicing the invention can be of the immune or non-immune type. Immune specific binding pairs are exemplified by antigen/antibody systems or hapten/anti-hapten systems. The antibody member of the binding pair, whether polyclonal, monoclonal or an immunoreactive fragment thereof, can be produced by customary means familiar to those skilled in the art. The terms immunoreactive antibody fragment or immunoreactive fragment mean fragments which contain the binding region of the antibody. Such fragments can be Fab-type fragments which are defined as fragments devoid of the Fc portion, e.g., Fab, Fab' and F(ab')$_2$ fragments, or can be called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethylamino)benzoic acid (BMAB), etc.

The invention can be used to determine the presence and amount of biological materials in solution, such as antibodies, antigens, DNA fragments, enzymes, hormones, other proteins and other substances naturally present in human or animal body fluids or in solutions generated by man.

The lanthanide metal ion used in this invention can comprise any lanthanide known to be suitable in time resolved fluorescence. Preferred lanthanide metal ions include europium (Eu$^{+3}$) and terbium (Tb$^{+3}$), although others, such as dysprosium (Dy$^{+3}$) and samarium (Sm$^{+3}$), also can be used.

The chelating agent used to form the chelate carrier complex with the lanthanide metal ion and biological material to be measured can be any agent known in the literature as suitable for forming a complex with lanthanide ions with a formation constant of at least $10^{11}$. Desirably the formation constant is within the range of $10^{14}$ to $10^{25}$. Useful compounds include those incorporating diethylenetriamine pentaacetate (DTPA), trans-1,2-diaminocyclohexanetetraacetate (DCTA), ethylenediaminetetraacetate (EDTA), N-hydroxyethylenediaminotriacetate (HEDTA), nitriloacetate (NTA), triethylenetetraaminehexaacetate (TTHA), 1,4,8,11-tetraazcyclotetradecane-1,4,8,11-tetraacetate (TETA), 1,4,7,10-tetraazacyclododecane (DOTA), 2,6-dipicolinate (bis or tris chelate) (DPA), iminodiacetate (bis or tris chelate), macrocyclic chelates as described in U.S. Pat. No. 5,373,093, aminepolycarboxylate chelates as described in U.S. Pat. No. 5,622,821, aminopolyanions as described in U.S. Pat. No. 4,808,541, aminepolyanions as described in U.S. Pat. No. 5,256,535, cryptates as described in U.S. Pat. No. 5,534,622, phenanthroline polyanions as described in U.S. Pat. No. 5,262,526, and chelates as described in U.S. Pat. Nos. 4,801,722; 4,837,169; 4,637,988; and 5,523,402.

The disclosures of the foregoing patents are incorporated herein by reference.

Preferred compounds include maleimide, succinimidyl or isothiocyanate (ITC-) derivatives of DTPA, phenyl-EDTA, or benzyl EDTA. Other suitable compounds include the N1-isothiocyanate derivative of benzyl DTTA, DTPA derivatives containing carbostyril 124 or coumarins and analogous derivatives of TTHA. The preferred compounds can be fluorescent or non-fluorescent.

Once the chelate complex is formed by coupling the lanthanide metal ion to the biological substance through the selected chelate forming compound in solution, the lanthanide metal ion is separated from the chelating compound by adding to the solution a buffer solution comprising a detergent, an enhancer reagent and a polyanion. The polyanion is added in excess to the carrier chelate, which ensures that the lanthanide is quickly and completely released from the carrier chelate and can associate with the enhancer reagent. "Added in excess" as used herein means that the concentration of the polyanion is at least 1,000 times the concentration of the carrier chelate, preferably in the range of 1–100 mM, dependent on the selected polyanion.

Useful polyanions are those compounds comprising at least two acid functional groups derived from carbon, phosphorus, nitrogen and/or sulfur. A variety of groups are suitable, including citrate, sulfosuccinate, oxalate, dinitrobenzoate, phosphonoformate, and pyrophosphosphate. Generally, the polyanions used in the method of this invention will have a $K_1$ formation constant with lanthanides of no more than $10^{11}$, preferably within the range of $10^2$ to $10^{10}$.

The polyanions useful in the method of this invention have a general formula

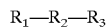

wherein
each of $R_1$ and $R_3$, which can be the same or different, is selected from the group consisting of —OPO$_3$H$_2$, —NO$_2$, —SO$_3$H, —NO, —COOH, —PO$_3$H$_2$ and —SH;

and $R_2$ is an optional group which, if present, is selected from the group consisting of
a linear alkyl chain comprising from 1–10 carbons, wherein one or more of the carbons optionally carries a substituent selected from the group consisting of —OH, —COOH, —NH$_2$, —SH, —OPO$_3$H$_2$, —NO$_2$, acetamido and —SO$_3$H,
a cyclic alkyl chain comprising from about 4–10 carbons, and optionally a hetero atom selected from the group consisting of nitrogen, oxygen and sulfur, wherein one or more of the carbons or the heteroatom optionally carries a substituent selected from the group consisting of —OH, —COOH, —NH$_2$, —SH, —OPO$_3$H$_2$, —NO$_2$, acetate and —SO$_3$H,
a linear carbon chain comprising from 2 to 6 carbons, characterized by one or more double bonds between 2 adjacent carbons, wherein one or more of the carbons in the chain optionally carries a substituent selected from the group consisting of —OH, —COOH, —NH$_2$, keto, acetate, —SH, —OPO$_3$H$_2$, —NO$_2$, and —SO$_3$H and alkyl-carb
a phenyl, benzyl or pyridyl group, one or more of the carbons of which optionally carries a substituent selected from the group consisting of —OH, keto, —COOH, —NH$_2$, —SH, —OPO$_3$H$_2$, —SO$_3$H and —NO$_2$, —(CH$_2$)$_m$—X—(CH$_2$)$_n$—, wherein m and n independently are each a number between 0 and 10, any carbon in the —(—CH$_2$)$_m$— or —(CH$_2$)$_n$— alkyl chain optionally can carry a substituent selected from the group consisting of —OH, —COOH, —NH$_2$, —SH, acetamido, —OPO$_3$H$_2$ and —SO$_3$H, and X is selected from the group consisting of —CO—, PO$_4$H, phenyl, benzyl, -pyridinyl, —N—, —S— or —O—. X also can carry one or more optional substituents selected from —OH, —COOH, —NH$_2$, —SH, —OPO$_3$H$_2$, —NO$_2$, —Cl, —CH$_3$, —(CH$_2$)$_y$NH$_2$, —(CH$_2$)$_z$CH$_3$, keto, phenyl, oenzyl, pyridyl, acetamido and —SO$_3$H, where y and z are numbers between 1 and 10.

Specific compounds useful as polyanions in the present invention include the following:

1,2-cyclohexanedicarboxylic acid
1,3,5-cyclohexane tricarboxylic acid
4,5-dihydroxy-1,3-benzenedisulfonic acid (tiron)
acetamidoiminodiacetic acid
alpha-ketoglutaric acid
3-ketoglutaric acid
aspartic acid
cis-aconitic acid
trans-aconitic acid
chelidamic acid
citric acid
cyclohexanehexacarboxylic acid
cysteine
diglycolic acid
D-tartaric acid
L-tartaric acid
ethanedisulfonic acid
fumaric acid
gamma-carboxyglutamic acid
glutamic acid
glutaric acid
iminodiacetic acid
isocitric acid
Kemp's triacid
maleic acid
malonic acid
mercaptosuccinic acid
meso-tartaric acid
methanedisulfonic acid
methylmalonic acid
nitrilotriacetic acid
oxalic acid
phthalic acid
phytic acid
propanetricarboxylic acid
pyridinedicarboxylic acid
pyromellitic acid
phosphonoformic acid
pyrophosphoric acid
sulfosuccinic acid
THF-2r,3t,4y,5c-tetracarboxylate
trimellitic acid
1,2,4,5-benzene-tetracarboxylic acid
1,2,3,4,5-pentacarboxy cyclopentane
3-amino-1-hydroxypropane-1,1-diphosphonic acid (pamidronic acid)
ethane-1-hydroxy-1,1-diphosphonic acid (etidronic acid)
dichloromethanediphosphonic acid (clodronic acid)
tripolyphosphate
persulfate
2,4-dinitrobenzoate
nitrosylsulfuric and
nitroterephthalate

TABLE 1

Examples of Polyanion Structures in the R$_1$—R$_2$—R$_3$ format

| Polyanion | R$_1$ | R$_2$ | R$_3$ |
|---|---|---|---|
| 2-ketoglutarate | HO$_2$C— | —CH$_2$CH$_2$C(=O)— | —CO$_2$H |
| oxalate | HO$_2$C— | — | —CO$_2$H |
| 3-ketoglutarate | HO$_2$C— | —CH$_2$C(=O)CH$_2$— | —CO$_2$H |
| Nitroterephthalic | HO$_2$C— | 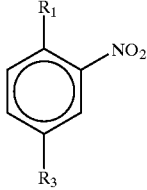 | —CO$_2$H |
| aspartate | HO$_2$C— | —CH$_2$CH(NH$_2$)— | —CO$_2$H |
| glutamate | HO$_2$C— | —CH$_2$CH$_2$CH(NH$_2$)— | —CO$_2$H |
| iminodiacetate | HO$_2$C— | —CH$_2$NHCH$_2$— | —CO$_2$H |
| isocitrate | HO$_2$C— | CH$_2$CH(CO$_2$H)CH(OH)— | —CO$_2$H |
| maleate, fumarate | HO$_2$C— | —CH=CH— | —CO$_2$H |
| citrate | HO$_2$C— | —CH$_2$—C(OH)(CO$_2$H)—CH$_2$— | —CO$_2$H |
| Methanedisulfonate | HO$_3$S— | —CH2— | —SO$_3$H |
| 4,5-dihydroxy-1,3-benzenedisulfonate | HO$_3$S— | 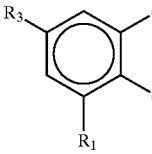 | —SO$_3$H |

TABLE 1-continued

Examples of Polyanion Structures in the $R_1$—$R_2$—$R_3$ format

| Polyanion | $R_1$ | $R_2$ | $R_3$ |
| --- | --- | --- | --- |
| mercaptosuccinate | $HO_2C$— | —$CH_2$—CH(SH)— | —$CO_2H$ |
| phthalate | $HO_2C$— | 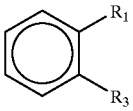 | —$CO_2H$ |
| malonate | $HO_2C$— | —$CH_2$— | —$CO_2H$ |
| sulfosuccinate | $HO_2C$— | —$CH_2$—CH($SO_3H$)— | —$CO_2H$ |
| tartarate (all isomers) | $HO_2C$— | —CH(OH)—CH(OH)— | —$CO_2H$ |
| pyrophosphate | $H_2O_3PO$— | — | —$PO_3H_2$ |
| propanetricarboxylate | $HO_2C$— | —CH($CO_2H$)— | —$CO_2H$ |
| methylmalonate | $HO_2C$— | —CH($CH_3$)— | —$CO_2H$ |
| 2,4-dinitrobenzoate | $HO_2C$— | 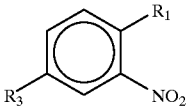 | —$NO_2$ |
| phosphonoformate | $H_2O_3PO$— | — | —$CO_2H$ |
| ethanedisulfonic | $HO_3S$— | —$CH_2$—$CH_2$— | —$SO_3H$ |
| aconitate(cis and trans) | $H_2OC$— | —CH=C($CH_2CO_2H$)— | —$CO_2H$ |
| 1,2-cyclohexane dicarboxylate | $HO_2C$— | 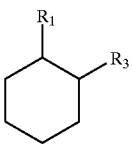 | —$CO_2H$ |
| 1,3,5-cyclohexane tricarboxylate | $HO_2C$— | 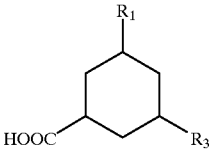 | —$CO_2H$ |
| persulfate | $HO_3S$—O— | — | —O—$SO_3H$ |
| cyclohexane hexacarboxylate | $HO_2C$— | 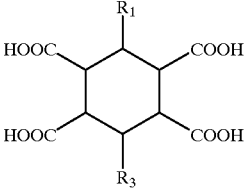 | —$CO_2H$ |
| 1,2,4,5-benzene-tetracarboxylate | $HO_2C$— | 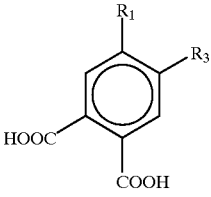 | —$CO_2H$ |
| cysteine | HS— | —$CH_2$—CH($NH_2$)— | —$CO_2H$ |
| gamma-carboxyglutamate | $HO_2C$— | CH(COOH)—$CH_2$—CH($NH_2$)— | —$CO_2H$ |

TABLE 1-continued

Examples of Polyanion Structures in the $R_1$—$R_2$—$R_3$ format

| Polyanion | $R_1$ | $R_2$ | $R_3$ |
|---|---|---|---|
| tripolyphosphate | $H_2O_3P-$ | $-O-P(=O)(OH)-O-$ | $-PO_3H_2$ |
| acetamidoiminodiacetate | $HO_2C-$ | $-CH_2N(acetamido)CH_2-$ | $-CO_2H$ |
| Kemp's triacid | $HO_2C-$ | cyclohexane with $R_1$, $R_3$, and $CH_2COOH$ substituents | $-CO_2H$ |
| chelidamate | $HO_2C-$ | 4-oxo-pyridine with $R_1$, $R_3$ at 2,6 positions | $-CO_2H$ |
| pyridinedicarboxylate | $HO_2C-$ | pyridine with $R_1$, $R_3$ at 2,6 positions | $-CO_2H$ |
| THF-tetracarboxylate | $HO_2C-$ | tetrahydrofuran with $R_1$, COOH, $R_3$, HOOC substituents | $-CO_2H$ |
| trimellitate | $HO_2C-$ | benzene ring with $R_1$, COOH, $R_3$ substituents | $-CO_2H$ |
| pentacarboxycyclopentane | $HO_2C-$ | cyclopentane with $R_1$, COOH, $R_3$, HOOC, COOH substituents | $-CO_2H$ |
| nitrosylsulfate | $O=N-$ | — | $-SO_3H$ |
| pamidronate | $H_2O_3PO-$ | $-C(OH)(C_2H_4NH_2)-$ | $-OPO_3H_2$ |
| etidronate | $H_2O_3PO-$ | $-C(OH)(CH_3)-$ | $-OPO_3H_2$ |
| clodronic | $H_2O_3PO-$ | $-C(Cl)_2-$ | $-OPO_3H_2$ |

Other compounds meeting the requirements of the general formula set forth above also can be used in the method of this invention. Although most of the listed compounds generally are considered inhibitors of lanthanide fluorescence enhancement, it has been found that at selected pH and concentration values these polyanions facilitate the rapid enhancement of lanthanide fluorescence.

The polyanion compound facilitates dissociation of the lanthanide metal ion from the carrier chelate and allows its reassociation with enhancer reagents that are capable of energy transfer to the lanthanide, causing the lanthanide to become intensely fluorescent. Suitable enhancer reagents can comprise β-diketones, such as α or β-naphthyltrifluoroacetone (α- or β-NTA), thenoyltrifluoroacetone (TTA), 1-naphthyltrifluoroacetone, pivaloyltrifluoroacetone, benzoyl trifluoroacetone, 2-furoyltrifluoroacetone, or 1,1,1,2,2-pentafluoro-6,6-dimethyl-3,5-heptanedione. Synergistic compounds known as Lewis bases, such as trioctylphosphine oxide (TOPO), also can be present but are not required. Other suitable enhancer reagents are known in the art.

Also included in the solution is a surfactant or detergent, such as TRITON or TWEEN, and other compounds known in the art which reduce surface tension and assist in solubilizing the reagents used in the method of the invention, including NP-40, CTAB, zwittergent, Brij and lauryl sulfate.

Figure 4:
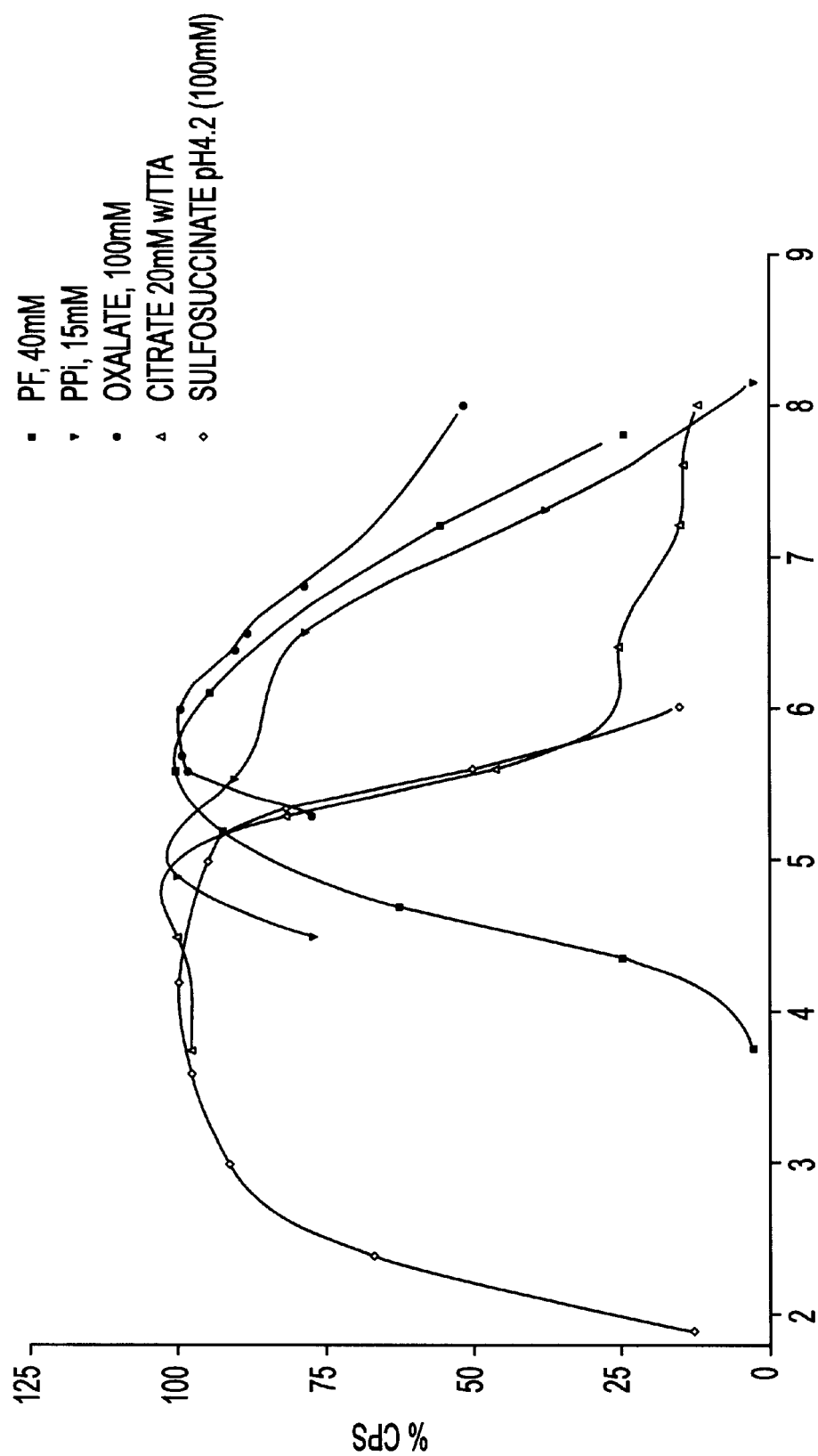
FIG. 4 is a graph showing pH optima for selected polyanion enhancement solutions.

The polyanion, detergent and enhancer reagent are provided in a buffer solution having a pH in the range of 3.5 to about 11.5, with a range of about 3.8 to about 10 being preferred and a range of about 4 to about 8 being more preferred. The desirable pH of a particular solution depends upon the polyanion chosen as the dissociation agent and the particular enhancer reagent present. Suitable buffers include, but are not limited to, Tris, borate, MOPS, imidazole, PIPES, carbonate and MES. Depending on the pKa of the polyanion, the polyanion also can contribute buffering capacity. The range of some suitable pH values is illustrated in FIG. 4, which is a graph showing optimal pH values for various enhancement solutions. Determining an optimal pH and optimal polyanion concentration for a desired solution can be determined by one of skill in the art using routine experimentation.

Several examples of enhancement solutions that are preferred for the method of this invention include:

a) about 50–120 mM oxalate, about 10–50 μM β-NTA, about 50–400 μM TOPO, about 0.1% Triton X-100, and about 10 mM imidazole, pH about 5.3–6.3;

b) about 20–60 mM phosphonoformate, about 10–50 μM β-NTA, about 50–400 μM TOPO, about 0.1% Triton X-100, and about 10 mM MES, pH about 5.1–6.1;

c) about 5–10 mM pyrophosphate, about 10–50 μM β-NTA, about 50–400 μM TOPO, about 0.1% Triton X-100, and about 10 mM MES, pH about 4.7–5.7;

d) about 10–20 mM citrate, about 10–50 μM β-NTA, about 50–400 μM TOPO, about 0.1% Triton X-100, and about 10 mM imidazole, pH about 6.0–7.0;

e) about 50–100 mM oxalate, about 10–50 μM β-NTA, about 5–20 μM thenoyltrifluoroacetone (TTA), about 50–400 μM TOPO, about 0.1% Triton X-100, and about 10 mM imidazole, pH about 6.3–7.3; and f) about 50–150 mM sulfosuccinate, about 10–50 μM β-NTA, about 50–400 μM TOPO, about 0.1% Triton X-100, about 10 mM MES; pH about 3.7–4.7.

Preferred enhancement solutions include:

a) about 80–120 mM oxalate, about 20–40 μM β-NTA, about 50–100 μM TOPO, about 0.1% Triton X-100, and about 10 mM imidazole, pH 5.5–6.1;

b) about 30–50 mM phosphonoformate, about 20–40 μM β-NTA, about 50–100 μM TOPO, about 0.1% Triton X-100, and about 10 mM MES; pH about 5.3–5.9;

c) about 7–10 mM pyrophosphate, about 20–40 μM β-NTA, about 50–100 μM TOPO, about 0.1% Triton X-100, and about 10 mM MES; pH about 4.9–5.5;

d) about 12–18 mM citrate, about 20–40 μM β-NTA, about 50–100 μM TOPO, about 0.1% Triton X-100, and about 10 mM imidazole; pH about 6.2–6.8;

e) about 65–85 mM oxalate, about 20–40 μM β-NTA, about 5–15 μM thenoyltrifluoroacetone (TTA), about 50–100 μM TOPO, about 0.1% Triton X-100, and about 10 mM imidazole; pH about 6.5–7.1; and f) about 75–125 mM sulfosuccinate, about 20–40 μM β-NTA, about 50–100 μM TOPO, about 0.1% Triton X-100, about 10 mM MES, pH about 3.9–4.5.

Preferred lanthanide metal ions in each of the preceding examples are europium and terbium.

The method of this invention is advantageous in that it allows for the rapid and complete dissociation of the lanthanide metal ion from the chelate complex and subsequent rapid reassociation with the enhancer reagent. Measurement of the resulting fluorescence of the lanthanide metal ion thus can be determined quickly (within 5–30 minutes) and with a high accuracy and fluorescent intensity.

The invention is further described and illustrated in the following examples, which are not intended to be limiting.

EXAMPLE 1

HIV-1 p24 ELISA with TRF Detection

The tissue culture procedure in an HIV-1 p24 ELISA kit was carried out with a modification to allow time resolved fluorescence determination (Product #NEK-050, NEN Life Science Products, Inc.). The p24 positive control, 200 ng/mL, was diluted into recalcified human serum to obtain standards between 0.0 and 1024 pg/mL. Each standard was assayed in paired sets of triplicate determinations. To wells (NEK-03, NEN Life Science Products, Inc.) coated with monoclonal antibody to HIV-1 p24 were added 200 μL of standard and the wells were incubated for 2 hours at 37°. The wells then were washed with wash buffer (Dulbecco's 1× PBS plus 0.05% Tween-20) six times. One hundred μL of biotinylated detector antibody, a rabbit polyclonal anti-p24 antibody in PBS containing animal sera, casein, and non-reactive human serum, were added to each well. The wells were sealed and incubated for 1 h at 37° and then washed six times with PBS-Tween-20. A streptavidin-europium conjugate (0.1 mg/mL, ~8 Eu per streptavidin via benzyl-EDTA chelate) was diluted 1:1000 into PBS containing 0.01% bovine serum albumin and 0.05% Tween-20 and added to each well (100 uL/well). The wells were sealed and incubated for 30 minutes at 22° C. and then washed six times with 10 mM Tris-HCl pH 7.4, 150 mM NaCl, 0.05% Tween-20. To one triplicate set an enhancement solution comprising 20 μM 2-naphthoyl trifluoroacetone, 400 μM triocytlphosphine oxide, 75 mM citrate, 25 mM imidazole pH 6.5, and 0.1% Triton X-100 was added. To the second triplicate set an enhancement solution comprising 20 uM 2-naphthoyl trifluoroacetone, 400 μM triocytlphosphine oxide, 50 mM L-malate, 25 mM imidazole pH 6.0, and 0.1% Triton X-100 was added. Both sets were incubated for 30 minutes and read on a DELFIA 1234 time-resolved fluorimeter (340 nM excitation, 615 nM emission, 400 μsec delay, 400 μsec count window, 1000 μsec/flash cycle). Data is presented as counts per second (cps). The blanks (~700 cps) were subtracted from each determination before graphing.

Figure 1B:
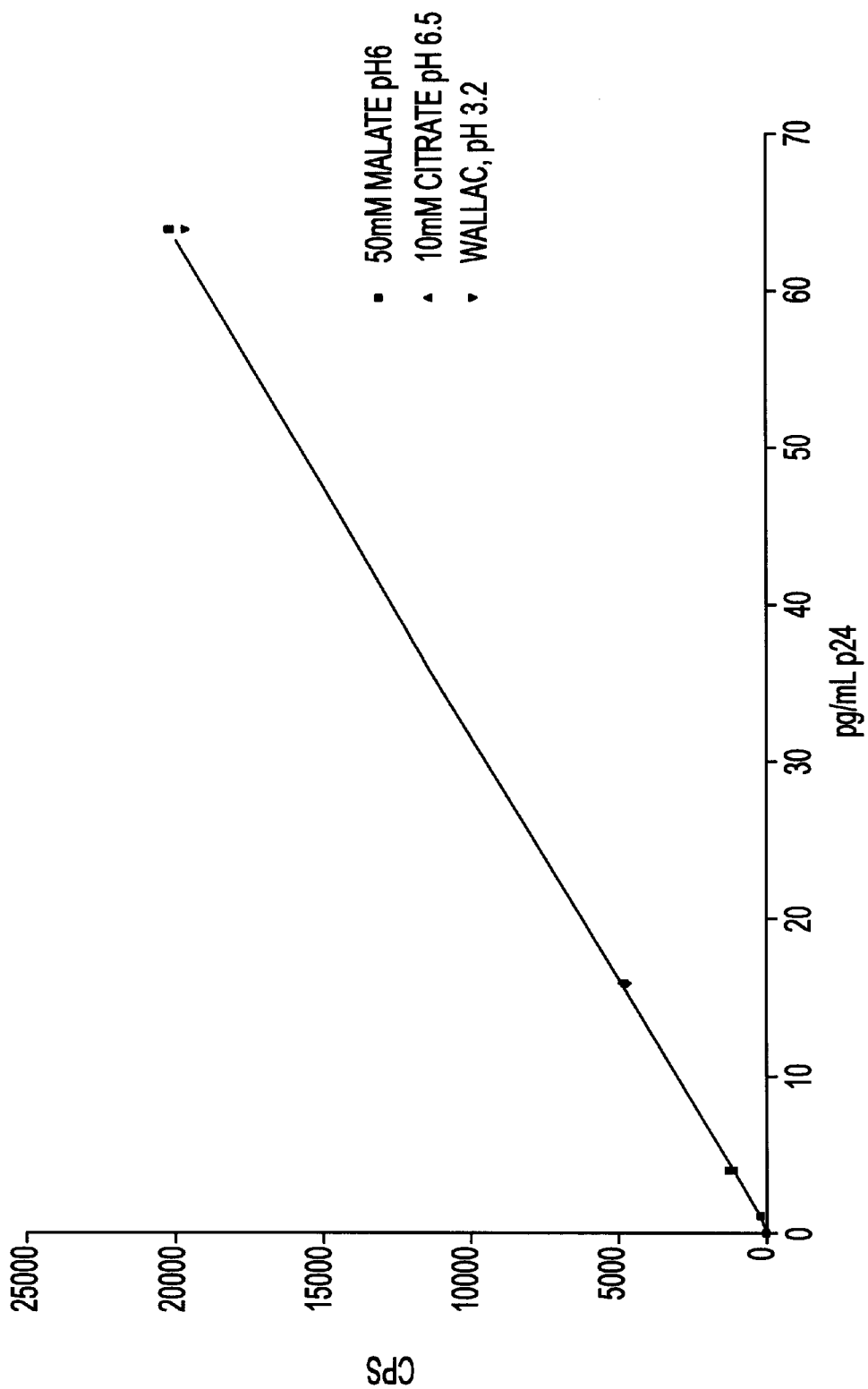

The results are shown in Tables 1A and 1B below and in FIGS. 1A and 1B. The sensitivity shown is 1 μg/mL with a dynamic range from 0.0 to 1000 pg/mL.

TABLE 1A

| X Values p24 (pg/mL) X | A malate Y | B citrate Y |
|---|---|---|
| 1 | 0.0 | 0.0 | 0.0 |
| 2 | 1.0 | 311.0 | 277.0 |
| 3 | 4.0 | 1326.0 | 1186.0 |
| 4 | 16.0 | 4931.0 | 5015.0 |
| 5 | 64.0 | 20118.0 | 20049.0 |
| 6 | 256.0 | 75609.0 | 73524.0 |
| 7 | 1024.0 | 252835.0 | 255220.0 |

TABLE 1B

| X Values p24 (pg/mL) X | A malate Y | B citrate Y |
|---|---|---|
| 1 | 0.0 | 0.0 | 0.0 |
| 2 | 1.0 | 311.0 | 277.0 |
| 3 | 4.0 | 1326.0 | 1186.0 |
| 4 | 16.0 | 4931.0 | 5015.0 |

EXAMPLE 2

Enhancement Signal Stability

Bovine serum albumin (BSA) was labeled with the NHS ester of diethylenetriaminepentaacetate-Eu (DTPA-Eu) at a level of ~5 Eu per molecule of BSA. The BSA-Eu was purified by size exclusion chromatography (Sephadex G-25). 5 μL of the BSA-Eu conjugate (~100,000 cpm after enhancement) were added to microplate wells containing 195 μL of one of the two selected enhancement solutions described below (n=5). At selected time intervals the wells were counted in a DELFIA time resolved fluorimeter as in Example 1. The signal obtained at 45 minutes was set at 100%. The enhancement solutions were either oxalate based or pyrophosphate based. The oxalate-based enhancement solution contained 50 mM oxalate, 20 μM 2-naphthoyltrifluoroacetone, 50 μM trioctylphosphine oxide, 25 mM imidazole pH 5.9, and 0.1% Triton X-100. The pyrophosphate-based enhancement solution contained 7.5 mM sodium pyrophosphate, 20 μM 2-naphthoyltrifluoroacetone, 50 μM trioctyl phosphine oxide, 25 mM MES pH 5.0, and 0.1% Triton X-100. For both enhancement solutions, signal stability was at least 24 hours with initial rapid development of signal (~30 minutes).

Figure 2:
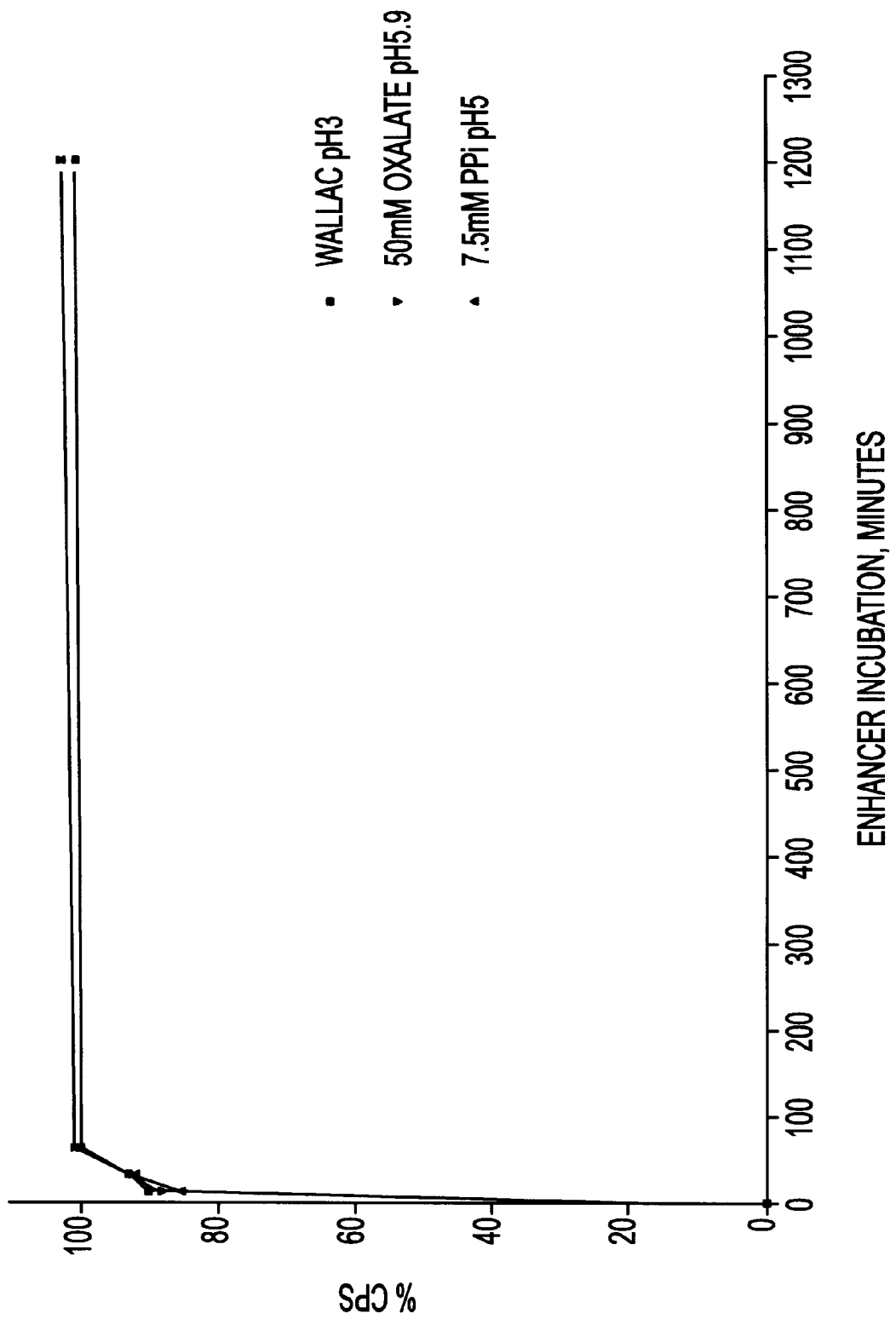
FIG. 2 is a graph showing enhancement of signal stability.

Results are shown in Table 2 below and in FIG. 2.

TABLE 2

| X Values minutes X | A pyrophosphate Y | B oxalate Y |
|---|---|---|
| 1 | 0.0 | 0.0 | 0.0 |
| 2 | 10.0 | 85.0 | 88.0 |
| 3 | 30.0 | 92.0 | 93.0 |
| 4 | 60.0 | 101.0 | 101.0 |
| 5 | 1200.0 | 103.0 | 103.0 |

EXAMPLE 3

Optional Polyanion Concentration Dependence at Selected pH Values

5 μL of streptavidin-Eu (diluted so that 5 μL gives ~100,000 cpm when enhanced) were added to microplate wells in triplicate with 195 μL of a selected enhancement solution, the solutions containing varying concentrations of a polyanion enhancer component (citrate, phosphonoformate, oxalate or sulfosuccinate). After a 30 minute incubation at room temperature, the plate was read on a DELFIA 1234 time resolved fluorimeter as in Example 1. The highest reading for each curve was taken as 100%. The maximum signals obtained for all cures were all within ±5%. All enhancement solutions contained 20 μM naphthoyltrifluoroacetone, 50 μM trioctylphosphine oxide and 0.1% Triton X-100 plus the polyanion at the selected concentration. The citrate-based enhancer was used at pH 7.25, the phosphonoformate-based enhancer was used at pH 5.6, the oxalate-based enhancer was used at pH 7 and the sulfosuccinate-based enhancer was used at pH 4.2. Depending upon the polyanion selected, an optimal concentration can be determined at each selected pH.

Figure 3:
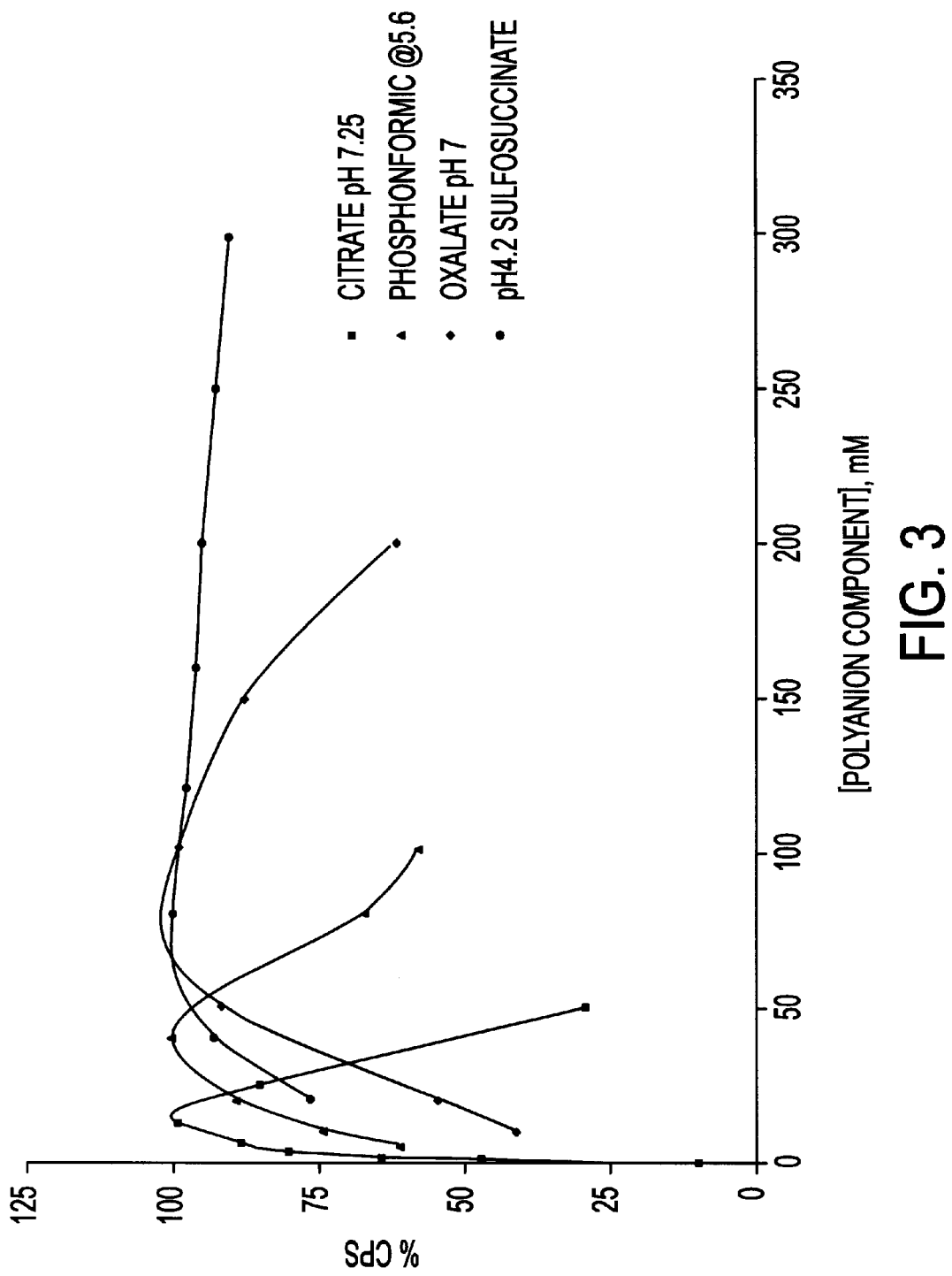
FIG. 3 is a graph showing polyanion concentration dependence at selected pH values.

The results are shown in Table 3 below and in FIG. 3.

TABLE 3

| X Values [polyacid], m X | A citrate Y | B phosphono-formate Y | C oxalate Y | D sulfosuccinate Y |
|---|---|---|---|---|
| 1 | 0.0 | 10.0 | | | |
| 2 | 0.8 | 47.0 | | | |
| 3 | 1.6 | 64.0 | | | |
| 4 | 3.1 | 80.0 | | | |
| 5 | 5.0 | | 61.0 | | |
| 6 | 6.3 | 88.0 | | | |
| 7 | 10.0 | | 74.0 | 41.0 | |
| 8 | 12.5 | 99.0 | | | |
| 9 | 20.0 | | 89.0 | 54.0 | 76.20 |
| 10 | 25.0 | 85.0 | | | |
| 11 | 40.0 | | 100.0 | | 92.80 |
| 12 | 50.0 | 29.0 | | 91.5 | |
| 13 | 80.0 | | 67.0 | | 100.0 |
| 14 | 100.0 | | 58.0 | 99.0 | |
| 15 | 120.0 | | | | 97.40 |
| 16 | 150.0 | | | 87.0 | |
| 17 | 160.0 | | | | 95.5 |
| 18 | 200.0 | | | 61.0 | 94.5 |
| 19 | 250.0 | | | | 91.90 |
| 20 | 300.0 | | | | |

EXAMPLE 4 pH Optima for Selected Polvanion-based Enhancement Solutions

5 μL of streptavidin-Eu (diluted so that 5 μL gives ~100,000 cpm when enhanced) were added in triplicate to microplate wells in triplicate with 195 uL of selected enhancement solutions formulated at different pH values. After 30 minutes of incubation at room temperature, the wells were counted on a DELFIA 1234 time resolved fluorimeter as in Example 1. The highest reading for each curve was taken as 100%. The maximum signals obtained for all curves were within ±5%. The following enhancement solutions were used at the indicated pH values:

40 mM phosphonoformate, 20 μM β-NTA, 50 μM TOPO and 0.1% Triton X-100;

15 mM pyrophosphate, 20 μM β-NTA, 50 μM TOPO and 0.1% Triton X-100;

75mM oxalate, 15 μM β-NTA, 5 μM TTA, 50 μM TOPO and 0.1% Triton X-100;

20 mM citrate, 20 μM TTA, 50 μM TOPO and 0.1% Triton X-100; and 100 mM sulfosuccinate, 20 μM β-NTA, 50 μM TOPO and 0.1% Triton X-100.

The results are shown in Table 4 below and in FIG. 4. An optimal pH value was determined for each of the polyanion and enhancer reagent(s) used.

TABLE 4

| x values pH X | A Phosphono-formate Y | B Pyrophos-phate Y | C Citrate Y | D Sulfo-succinate Y | E Oxalate + TTA Y |
|---|---|---|---|---|---|
| 1  1.90 |  |  |  | 13.0 |  |
| 2  2.40 |  |  |  | 67.0 |  |
| 3  3.00 |  |  |  | 91.5 |  |
| 4  3.60 |  |  |  | 98.0 |  |
| 5  3.75 | 3.0 |  | 98.0 |  |  |
| 6  4.10 |  |  |  |  | 2.7 |
| 7  4.20 |  |  |  | 100.0 |  |
| 8  4.33 | 25.0 |  |  |  |  |
| 9  4.50 |  | 77.0 | 100.0 |  | 15.5 |
| 10  4.70 | 62.6 |  |  |  |  |
| 11  4.90 |  | 100.0 |  |  |  |
| 12  5.00 |  |  |  | 94.40 |  |
| 13  5.20 | 92.0 |  |  |  |  |
| 14  5.30 |  |  | 81.5 |  | 71.5 |
| 15  5.35 |  |  |  | 81.20 |  |
| 16  5.40 |  |  |  |  |  |
| 17  5.54 |  | 90.0 |  |  |  |
| 18  5.60 | 100.0 |  | 46.0 | 50.0 |  |
| 19  5.80 |  |  |  |  | 78.7 |
| 20  6.00 |  |  |  | 15.0 |  |
| 21  6.10 | 94.0 |  |  |  |  |
| 22  6.30 |  |  |  |  | 100.0 |
| 23  6.40 |  |  | 25.0 |  |  |
| 24  6.50 |  | 78.0 |  |  |  |
| 25  7.10 |  |  |  |  | 92.9 |
| 26  7.20 | 55.0 |  | 14.5 |  |  |
| 27  7.30 |  | 37.0 |  |  |  |
| 28  7.50 |  |  |  |  | 85.8 |
| 29  7.60 |  |  | 14.0 |  |  |
| 30  7.80 | 24.0 |  |  |  |  |
| 31  8.00 |  |  |  | 11.6 |  |
| 32  8.15 |  | 2.0 |  |  |  |
| 33  8.30 |  |  |  |  | 83.4 |
| 34  9.30 |  |  |  |  | 75.4 |
| 35  10.10 |  |  |  |  | 68.2 |
| 36  11.30 |  |  |  |  | 65.9 |

We claim:

1. A method for the spectroscopic determination of chelated lanthanide metal ions bound to a marker which comprises:

(a) contacting chelated lanthanide metal ions bound to a marker with a buffered solution comprising a detergent, an enhancer reagent and a polyanion, wherein said buffer maintains the pH of the solution within the range of about 3.5 to about 11.5 and said polyanion is present in sufficient concentration such that said lanthanide metal ions disassociate from said marker and reassociate with said enhancer reagent, thereby transferring said lanthanide metal ions into a highly fluorescent form; and (b) determining the amount of lanthanide metal ion liberated from the marker as a measure of the amount of marker present in said solution by subjecting the solution to a short radiation pulse and detecting the fluorescence of the lanthanide metal ion after the fluorescence from any background source substantially has ceased.

2. The method of claim 1, wherein said polyanion comprises at least two acid functional groups derived from carbon, phosphorus, nitrogen, sulfur, or a combination thereof.

3. The method of claim 2, wherein said polyanion has the general formula $R_1—R_2—R_3$;

wherein each of $R_1$ and $R_3$, which can be the same or different, is selected from the group consisting of $—OPO_3H_2$, $—NO_2$, $—SO_3H$, $—NO$, $—PO_3H_2$, $—COOH$, and $—SH$;

and $R_2$ is an optional group which, if present, is selected from the group consisting of a linear alkyl chain comprising from 1–10 carbons, wherein one or more of the carbons optionally carries a substituent selected from the group consisting of $—OH$, $—COOH$, $—NH_2$, $—SH$, $—OPO_3H_2$, $—NO_2$, acetamido and $—SO_3H$, a cyclic alkyl chain comprising from about 4–10 carbons and optionally a hetero atom selected from the group consisting of nitrogen, oxygen and sulfur, wherein one or more of the carbons optionally carries a substituent selected from the group consisting of $—OH$, $—COOH$, $—NH_2$, acetate, $—SH$, $—OPO_3H_2$, $—NO_2$ and $—SO_3H$, a linear carbon chain comprising from 2 to 6 carbons, characterized by one or more double bonds between 2 adjacent carbons, wherein one or more of the carbons in the chain optionally carries a substituent selected from the group consisting of $—OH$, $—COOH$, $—NH_2$, keto, acetate, $—SH$, $—OPO_3H_2$, $—NO_2$ and $—SO_3H$, a phenyl, benzyl or pyridyl group, one or more of the carbons of which optionally carries a substituent selected from the group consisting of $—OH$, keto, $—COOH$, $—NH_2$, $—SH$, $—OPO_3H_2$, $—SO_3H$ and $—NO_2$, $—(CH_2)_m X—(CH_2)_n$, wherein m and n are numbers between 0 and 10, wherein any carbon in the alkyl chain optionally can carry a substituent selected from the group consisting of $—OH$, $—COOH$, $—NH_2$, $—SH$, acetamido, $—OPO_3H_2$ and $—SO_3H$, and X is selected from the group consisting of $—CO—$, $PO_4H$, phenyl, benzyl, -pyridinyl, $—N—$, $—S—$ or $—O—$; wherein X optionally can carry one or more substituents selected from $—OH$, $—COOH$, $—NH_2$, $—SH$, $—OPO_3H_2$, $—NO_2$, $—Cl$, $—CH_3$, $—(CH_2)_y NH_2$, $—(CH_2)_z CH_3$, keto, phenyl, benzyl, pyridyl, acetamido and $—SO_3H$ where y and z is each a number from 1 to 10.

4. The method of claim 3, wherein the polyanion comprises a citrate, sulfosuccinate, oxalate, dinitrobenzoate, phosphonoformate or pyrophosphate group.

5. The method of claim 3, wherein said polyanion comprises 1,2-cyclohexanedicarboxylic acid
1,3,5-cyclohexane tricarboxylic acid
4,5-dihydroxy-1,3-benzenedisulfonic acid (tiron)
acetamidoiminodiacetic acid
alpha-ketoglutaric acid
3-ketoglutaric acid
aspartic acid
cis-aconitic acid
trans-aconitic acid
citric acid
cyclohexanehexacarboxylic acid
cysteine
diglycolic acid
D-tartaric acid
L-tartaric acid
ethanedisulfonic acid fumaric acid
gamma-carboxyglutamic acid
sulfosuccinic acid
nitrilotriacetic acid
glutamic acid
glutaric acid
iminodiacetic acid
isocitric acid
Kemp's triacid
maleic acid
malonic acid
mercaptosuccinic acid
meso-tartaric acid
methanedisulfonic acid
methylmalonic acid
oxalic acid
phthalic acid
phytic acid
chelidamic acid
propanetricarboxyxlic acid
pyridinedicarboxylic acid
pyromellitic acid
phosphonoformic acid
THF-2r,3t,4y,5c-tetracarboxylate
trimellitic acid
1,2,3,4,5-pentacarboxy cyclopentane
pyrophsophoric acid
3-amino-1-hydroxypropane-1,1-diphosphonic acid
ethane-1-hydroxy-1,1-diphosphonic acid
dichloromethanediphosphonic acid
tripolyphosphate
persulfate
2,4-dinitrobenzoate
nitrosylsulfuric or
nitroterephthalate.

6. The method of claim 5, wherein said polyanion comprises oxalate, phosphonoformate, pyrophosphate, sulfosuccinate, dinitrobenzoate, or citrate.

7. The method of claim 1, 2 or 3, wherein said lanthanide metal is chelated with a chelating agent which forms a complex with said lanthanide metal ion and has a formation constant $K_1$ within the range of about $10^{11}$ to $10^{25}$.

8. The method of claim 7, wherein said chelating agent comprises diethylenetriamine pentaacetate (DTPA), trans-1,2-diaminocyclohexanetetraacetate (DCTA), ethylenediaminetetraacetate (EDTA), N-hydroxyethylenediaminotriacetate (HEDTA), nitriloacetate (NTA), triethylenetetraaminehexaacetate (TTHA), 1,4,8,11-tetraazcyclotetradecane-1,4,8,11-tetraacetate (TETA), 1,4,7,10-tetraazacyclododecane (DOTA), 2,6-dipicolinate (bis or tris chelate), bis-pyridine based macrocycles, or iminodiacetate (bis or tris chelate).

9. The method of claim 1, wherein said enhancer reagent comprises a β-diketone.

10. The method of claim 9, wherein said β-diketone comprises 2-naphthyltrifluoroacetone (2-NTA), 1-naphthyltrifluoroacetone, thenoyl-trifluoroacetone, pivaloyltrifluoroacetone, benzoyltrifluoroacetone, 2-furoyltrifluoroacetone or 1,1,1,2,2-pentafluoro-6,6-dimethyl-3,5- heptanedione.

11. The method of claim 1, wherein said detergent comprises TRITON, TWEEN, NP-40, CTAB, zwittergent, Brij, or laurylsulfate.

12. The method of claim 9, which further comprises a Lewis base.

13. The method of claim 12, wherein said Lewis base comprises trioctylphosphine oxide.

14. The method of claim 1, wherein said polyanion comprises about 50–120 mM oxalate and said enhancer reagent comprises about 10–50 μM β-NTA.

15. The method of claim 1, wherein said polyanion comprises about 20–60 μM phosphonoformate and said enhancer reagent comprises about 10–50 μM β-NTA.

16. The method of claim 1, wherein said polyanion comprises about 5–10 mM pyrophosphate and said enhancer reagent comprises about 10–50 μM β-NTA.

17. The method of claim 1, wherein said polyanion comprises about 10–20 mM citrate and said enhancer reagent comprises about 10–50 μM β-NTA.

18. The method of claim 1, wherein said polyanion comprises about 50–150 mM sulfosuccinate and said enhancer reagent comprises about 10–50 μM β-NTA.

19. The method of claim 14, 15, 16, 17, or 18, wherein said enhancer reagent further comprises about 50–400 μM trioctylphosphine oxide.

20. The method of claim 1, wherein said buffer comprises Tris, borate, MOPS, imidazole, PIPES, carbonate and MES.

21. The method of claim 1, wherein the lanthanide metal ion is a europium, terbium, dysprosium or samarium ion.

22. The method of claim 2, wherein said polyanion has a maximum formation constant $K_1$ of $10^{11}$ with selected lanthanide.

23. The method of claim 1, wherein the pH of the solution is maintained within the range of 3.8 to about 10.

24. The method of claim 1, wherein the pH of the solution is maintained within the range of 4 to 8.

25. A composition comprising lanthanide metal ion, a polyanion comprising at least two acid functional groups derived from carbon, phosphorus, nitrogen, sulfur or a combination thereof, and an enhancer reagent.

26. The composition of claim 25, wherein the polyanion has the general formula $$R_1—R_2—R_3;$$

wherein
each of $R_1$ and $R_3$, which can be the same or different, is selected from the group consisting of $—OPO_3H_2$, $—NO_2$, $—SO_3H$, $—NO$, $—PO_3H_2$, $—COOH$, and $—SH$;

and $R_2$ is an optional group which, if present, is selected from the group consisting of
a linear alkyl chain comprising from 1–10 carbons, wherein one or more of the carbons optionally carries a substituent selected from the group consisting of $—OH$, $—COOH$, $—NH_2$, $—SH$, $—OPO_3H_2$, $—NO_2$, acetamido and $—SO_3H$,
a cyclic alkyl chain comprising from about 4–10 carbons and optionally a hetero atom selected from the group consisting of nitrogen, oxygen and sulfur, wherein one or more of the carbons optionally carries a substituent selected from the group consisting of $—OH$, $—COOH$, $—NH_2$, acetate, $—SH$, $—OPO_3H_2$, $—NO_2$ and $—SO_3H$,
a linear carbon chain comprising from 2 to 6 carbons, characterized by one or more double bonds between 2 adjacent carbons, wherein one or more of the carbons in the chain optionally carries a substituent selected from the group consisting of $—OH$, $—COOH$, $—NH_2$, keto, acetate, $—SH$, $—OPO_3H_2$, $—NO$, and $—SO_3H$,
a phenyl, benzyl or pyridyl group, one or more of the carbons of which optionally carries a substituent selected from the group consisting of $—OH$, keto, $—COOH$, $—NH_2$, $—SH$, $—OPO_3H_2$, $—SO_3H$ and $—NO_2$, —(CH$_2$)$_m$X—(CH$_2$)$_n$, wherein m and n are numbers between 0 and 10, wherein any carbon in the alkyl chain optionally can carry a substituent selected from the group consisting of —OH, —COOH, —NH$_2$, —SH, acetamido, —OPO$_3$H$_2$ and —SO$_3$H, and X is selected from the group consisting of —CO—, PO$_4$H, phenyl, benzyl, - pyridinyl, —N—, —S— or —O—; wherein X optionally can carry one or more substituents selected from —OH, —COOH, —NH$_2$, —SH, —OPO$_3$H$_2$, —NO$_2$, —Cl, —CH$_3$, —(CH$_2$)$_y$ NH$_2$, —(CH$_2$)$_z$CH$_3$, keto, phenyl, benzyl, pyridyl, acetamido and —SO$_3$H where y and z is each a number from 1 to 10.

27. The composition of claim 26, wherein the polyanion comprises a citrate, sulfosuccinate, oxalate, dinitrobenzoate, phosphonoformate or pyrophosphate group.

28. The composition of claim 26, wherein said polyanion comprises
1,2-cyclohexanedicarboxylic acid
1,3,5-cyclohexane tricarboxylic acid
4,5-dihydroxy-1,3-benzenedisulfonic acid (tiron)
acetamidoiminodiacetic acid
alpha-ketoglutaric acid
3-ketoglutaric acid
aspartic acid
cis-aconitic acid
trans-aconitic acid
citric acid
cyclohexanehexacarboxylic acid
cysteine
diglycolic acid
D-tartaric acid
L-tartaric acid
ethanedisulfonic acid
fumaric acid
gamma-carboxyglutamic acid
sulfosuccinic acid
nitrilotriacetic acid
glutamic acid
glutaric acid
iminodiacetic acid
isocitric acid
Kemp's triacid
maleic acid
malonic acid
mercaptosuccinic acid
meso-tartaric acid
methanedisulfonic acid
methylmalonic acid
oxalic acid
phthalic acid
phytic acid
chelidamic acid
propanetricarboxyxlic acid
pyridinedicarboxylic acid
pyromellitic acid
phosphonoformic acid
THF-2r,3t,4y,5c-tetracarboxylate
trimellitic acid
1,2,3,4,5-pentacarboxy cyclopentane
pyrophsophoric acid
3-amino-1-hydroxypropane-1,1-diphosphonic acid
ethane-1-hydroxy-1,1-diphosphonic acid
dichloromethanediphosphonic acid
tripolyphosphate
persulfate
2,4-dinitrobenzoate
nitrosylsulfuric or
nitroterephthalate.

29. The composition of claim 25 or 26, wherein said enhancer reagent comprises a β-diketone.

30. The composition of claim 29, which further comprises a Lewis base.

31. The composition of claim 30, wherein said Lewis base comprises trioctylphosphine oxide.

32. The composition of claim 29, wherein said β-diketone comprises 2-naphthyltrifluoroacetone (2-NTA), 1-naphthyltrifluoroacetone, thenoyl-trifluoroacetone, pivaloyltrifluoroacetone, benzoyltrifluoroacetone, 2-furoyltrifluoroacetone or 1,1,1,2,2-pentafluoro-6,6-dimethyl-3,5-heptanedione.

33. The composition of claim 25, wherein said lanthanide metal ion is a europium, terbium, dysprosium or samrium ion.

* * * * *